United States Patent
McMichael

(10) Patent No.: US 9,682,058 B2
(45) Date of Patent: Jun. 20, 2017

(54) METHOD OF TREATING VIRAL INFECTIONS BY ADMINISTRATION OF ETHYL MERCURY OR THIOL DERIVATIVE THEREOF

(75) Inventor: John McMichael, Delanson, NY (US)

(73) Assignee: BEECH TREE LABS, INC., Delanson, NY (US)

( * ) Notice: Subject to any disclaimer, the term of this patent is extended or adjusted under 35 U.S.C. 154(b) by 1079 days.

(21) Appl. No.: 13/051,776

(22) Filed: Mar. 18, 2011

(65) Prior Publication Data

US 2011/0230554 A1 Sep. 22, 2011

Related U.S. Application Data

(60) Provisional application No. 61/315,727, filed on Mar. 19, 2010.

(51) Int. Cl.
*A61K 31/095* (2006.01)
*A61K 31/192* (2006.01)
*A61K 31/305* (2006.01)

(52) U.S. Cl.
CPC .......... *A61K 31/305* (2013.01); *A61K 31/095* (2013.01); *A61K 31/192* (2013.01)

(58) Field of Classification Search
CPC ... A61K 31/095; A61K 31/192; A61K 31/305
USPC ....................................... 514/496
See application file for complete search history.

(56) References Cited

U.S. PATENT DOCUMENTS

| | | | |
|---|---|---|---|
| 4,083,991 A * | 4/1978 | Manfuso, Jr. ................. | 514/496 |
| 4,521,405 A | 6/1985 | McMichael | |
| 4,803,991 A | 2/1989 | Alena et al. | |
| 4,880,626 A | 11/1989 | McMichael | |
| 5,753,624 A | 5/1998 | McMichael et al. | |
| 6,174,916 B1 | 1/2001 | McMichael | |
| 6,303,127 B1 | 10/2001 | McMichael et al. | |
| 7,196,058 B2 | 3/2007 | McMichael et al. | |
| 7,629,312 B2 | 12/2009 | McMichael | |
| 2004/0127409 A1 | 7/2004 | McMichael et al. | |
| 2005/0245502 A1* | 11/2005 | Keller ...................... | 514/211.07 |
| 2007/0148765 A1* | 6/2007 | Evans et al. ............... | 435/320.1 |
| 2009/0214510 A1 | 8/2009 | Nabel et al. | |
| 2009/0285819 A1 | 11/2009 | Li et al. | |
| 2010/0144602 A1 | 6/2010 | McMichael | |

OTHER PUBLICATIONS

Allan, "Motor proteins: A dynamic duo," *Current Biology*, 6(6):630-633 (1996).
Boylan et al., "A Molecular Genetic Analysis of the Interaction between the Cytoplasmic Dynein Intermediate Chain and the Glued (Dynactin) Complex," *Mol. Bio. of the Cell*, 11:3791-3803 (2000).
Covadonga et al., "African Swine Fever Virus Protein p54 Interacts with the Microtubular Motor Complex through Direct Binding to Light-Chain Dynein," *Jour. of Viro.*, 75(20):9819-9827 (2001).
Dohner et al., "Function of Dynein and Dynactin in Herpes Simplex Virus Capsid Transport," *Mol. Bio. of the Cell*, 13:2795-2809 (2002).
International Search Report for PCT/US11/29049, dated May 3, 2011.
Leopold et al., "Dynein- and Microtubule-Mediated Translocation of Adenovirus Serotype 5 Occurs after Endosomal Lysis," *Human Gene Therapy*, 11:151-165 (2000).
Machaty et al., "Complete Activation of Porcine Oocytes Induced by the Sulfhydryl Reagent, Thimerosal," *Bio. of Rep.*, 57:1123-1127 (1997).
Ploubidou et al., "Vaccinia virus infection disrupts microtubule organization and centrosome function," *The EMBO Jour.*, 19(15):3932-3944 (2000).
Rietdorf et al., "Kinesin-dependent movement on microtubules precedes actin-based motility of vaccinia virus," *Nature Cell Bio.*, 3:992-1000 (2001).
Sodeik et al., "Microtubule-mediated Transport of Incoming Herpes Simplex Virus 1 Capsids to the Nucleus," *The Jour. of Cell Bio.*, 136(5):1007-1021 (1997).
Suomalainen et al., "Adenovirus-activated PKA and p38/MAPK pathways boost microtubule-mediated nuclear targeting of virus," *The EMBO Jour.*, 20(6):1310-1319 (2001).
Suomalainen et al., "Microtubule-dependent Plus- and Minus End-directed Motilities are Competing Processes for Nuclear Targeting of Adenovirus," *The Jour. of Cell Bio.*, 144(4):657-672 (1999).
Vaughan et al., "Cytoplasmic Dynein Intermediate Chain Phosphorylation Regulates Binding to Dynactin," *The Jour. of Bio. Chem.*, 276(28):26171-26179 (2001).
Ward, "The longest micron; transporting poxviruses out of the cell," *Cellular Microbiology*, 7(11):1531-1538 (2005).
Written Opinion for PCT/US11/29049, dated May 3, 2011.
Ye et al., "The Herpes Simplex Virus 1 $U_L34$ Protein Interacts with a Cytoplasmic Dynein Intermediate Chain and Targets Nuclear Membrane," *Jour. of Vir.*, 74(3):1355-1363 (2000).

* cited by examiner

*Primary Examiner* — Yong Chong
(74) *Attorney, Agent, or Firm* — Marshall, Gerstein & Borun LLP

(57) ABSTRACT

Disclosed herein are methods of treating viral infections by administration of ethyl mercury or thiol derivative thereof in an amount effective to treat the viral infection.

8 Claims, 5 Drawing Sheets

METHOD OF TREATING VIRAL INFECTIONS BY ADMINISTRATION OF ETHYL MERCURY OR THIOL DERIVATIVE THEREOF

CROSS-REFERENCE TO RELATED APPLICATIONS

The present applications claims the benefit of priority to U.S. Provisional Application No. 61/315,727 filed Mar. 19, 2010, the disclosure of which is incorporated herein by reference in its entirety.

BACKGROUND OF THE INVENTION

Most DNA viruses replicate in the nucleus, which provides the cellular factors required for the amplification and transcription of the viral genomes and for posttranscriptional processing of the viral mRNA. This suggests that after crossing the plasma membrane or endocytic membrane, released viruses or their components must also traverse the cytoplasm to enter the nucleus.

The cytoplasm imposes a diffusion barrier caused by high viscosity and steric obstacles. Cytoplasmic solutes and macromolecules, along with the lattice-like mesh of microtubules, actin, and intermediate filament networks, restrict the free diffusion of macromolecular complexes larger than 500 kDa, indicating that virus-sized particles are unlikely to move efficiently through the cytosol by diffusion alone. It is likely that viruses would need to be actively transported during their cytoplasmic trafficking. Microtubules are polarized structures with a fast-growing plus end extending toward the cell periphery and a slow-growing minus end located at the centrosome or microtubule organizing center (MTOC), which is typically found in a perinuclear position. Directed transport of cellular components is linked to large complexes that form molecular motors. Cytoplasmic dynein and kinesin are known to mediate organelle movement in opposite directions along microtubules. Cytoplasmic dynein, a minus-end-directed, microtubule-based motor, is a multisubunit protein complex of 1,270 kDa consisting of two heavy chains (530 kDa), two or three intermediate chains (74 kDa), and a variable number of small subunits. The ATPase and microtubule motor domains are located within the dynein heavy chains, whereas the specific cargo-binding activity involves the intermediate chains and several classes of light chains (Boylan et al., Mol. Biol. Cell, 11:3791-3803, 2000 and Vaughan et al., J. Biol. Chem., 276:26171-16179, 2001). In many cases the microtubule-dependent transport of material is facilitated by the dynein activator protein dynactin, which mediates dynein binding to microtubules (Allan, Curr. Biol., 6:630-633, 1996). Dynein, in conjunction with dynactin, facilitates membrane transport from the early endosomes to late endosomes and lysosomes and from the endoplasmic reticulum to the Golgi apparatus.

The involvement of microtubules in cytoplasmic traffic has been reported for a number of viruses, and dynein-mediated transport has been described for adenovirus (Leopold et al., Hum. Gene ther., 11:151-165, 2000; Suomalainen et al., J. Cell Biol., 144:657-672, 1999 and Suomalainen et al., EMBO J., 20:1310-1319, 2001), human foamy virus (Saib et al., Virology, 228:263-268, 1997), herpes simplex virus type 1 (HSV-1) (Dohner et al., Mol. Biol. Cell, 13:2795-2809, 2002; Sodeik et al., J. Cell Biol., 136:1007-1021, 1997 and Ye et al., J. Virol., 74:1355-1363, 2000), and African swine fever virus (ASFV) (Alonso et al., J. Virol., 75:9818-9827, 2001). In addition, vaccinia virus exploits microtubules to enhance its exit from infected cells. Vaccinia virus particles, using microtubule plus-end-directed kinesin as a motor, are transported along microtubules from the perinuclear site of assembly to the site of exit at the plasma membrane (Ploubidou et al., EMBO J., 19:3932-3944, 2000 and Rietdorf et al., Nat. Cell Biol., 3:992-1000, 2001). Poxviruses due to their large size (approximately 250-300 µm) are dependent on active transport through microtubules for intracellular movement during infection (Ward, Cell Microbiol., 7:1531-1538, 2005).

Influenza virus vaccines, and their components, have been used to treat other virus infections, such as herpes virus infections, as reported in Lieberman, Clinical Ecology, 7(3): 51-54 (1990) and McMichael U.S. Pat. Nos. 4,521,405 and 4,880,626, all of which are incorporated herein by reference. Influenza vaccines induce a modified immune response such that symptoms were alleviated as a consequence of neutralizing the body's response to the infectious agent by stimulating suppressor T-cells. The T-cells in turn down-regulated effector cells and thus interrupted the allergic-type reaction induced by simultaneous lysis of many cells infected with the influenza virus. However, the results reported by McMichael and Lieberman attributed the anti-herpes virus effects of influenza virus vaccines to the presence of thimerosal, a preservative present in commercially available influenza virus vaccines, and not to a portion of the killed influenza virus, such as a surface antigen. Further, it has been discovered that the anti-herpes virus activity of influenza virus vaccines is attributable to the presence of thimerosal in the tested compositions and that herpes virus infections can be treated with thimerosal uncombined with or in the absence of influenza virus vaccine. Related to this is the disclosure of Manfuso, U.S. Pat. No. 4,803,991 which teaches the treatment of herpes virus infections by the topical administration of thimerosal, but does not teach or suggest the administration of thimerosal systemically.

In vitro assays with purified thimerosal demonstrate activity against herpes viruses (U.S. Pat. Nos. 4,803,991; 5,753,624; and 6,174,916). Of interest is the observation that when thimerosal is mixed in a test tube with herpes virus and is subsequently introduced into susceptible cells, viral propagation is not inhibited. This suggests that the anti-herpes viral activity of thimerosal is not by direct action on the virus. Further study shows that thiosalicylic acid and dithiodibenzoic acid, which are the breakdown products of thimerosal, do not provide antiviral activity in vivo although dithiodibenzoic acid indicated anti-herpes virus activity in vitro.

Adenoviruses most commonly cause respiratory illness; however, depending on the infecting serotype, they may also cause various other illnesses, such as gastroenteritis, conjunctivitis, cystitis, and rash illness. Symptoms of respiratory illness caused by adenovirus infection range from the common cold syndrome to pneumonia, croup, and bronchitis. Patients with compromised immune systems are especially susceptible to severe complications of adenovirus infection.

Although epidemiologic characteristics of the adenoviruses vary by type, all are transmitted by direct contact, fecal-oral transmission, and occasionally waterborne transmission. Some types are capable of establishing persistent asymptomatic infections in tonsils, adenoids, and intestines of infected hosts, and shedding can occur for months or years. Outbreaks of adenovirus-associated respiratory disease have been more common in the late winter, spring, and early summer; however, adenovirus infections can occur throughout the year.

Most infections with adenovirus result in infections of the upper respiratory tract. Adenovirus infections often show up as conjunctivitis, tonsillitis, an ear infection, or croup. Adenoviruses can also cause gastroenteritis (stomach flu). A combination of conjunctivitis and tonsillitis is particularly common with adenovirus infections. Some children (especially small ones) can develop adenovirus bronchiolitis or pneumonia, both of which can be severe. Other clinical syndromes associated with adenoviruses include, but are not limited to, pharyngitis, pharynconjunvtical fever, acute respiratory disease of recruits, pneumonia, follicular conjunctivitis, epidemic ketatoconjunctivitis, pertussis-like syndrome, acute hemorrhagic cystitis, acute infantile gastroenteritis, intussception and meningitis.

Papillomas are benign epithelial tumors that are caused by infection with the human papilloma virus (HPV). They are the most common benign neoplasms affecting the larynx and upper respiratory tract. Clinical manifestations associated with HPV include, but not are limited to, benign warts, juvenile laryngeal papillomatosis and epidermodysplasia verruciformis.

Pox viruses are generally enveloped and vary in shape depending upon the species but are generally shaped like a brick or as an oval form similar to a rounded brick because that are wrapped by the endoplasmic reticulum. The virion is exceptionally large (200 nm in diamete4 and 300 nm in length) and carries its genome in a single, linear double-stranded segment of DNA. In some embodiments, the pox virus is a varicella zoster virus. A varicella zoster viral infection is also known as the chicken pox. Chickenpox is often heralded by a prodrome of myalgia, nausea, fever, headache, sore throat, pain in both ears, complaints of pressure in head or swollen face, and malaise in adolescents and adults, while in children the first symptom is usually the development of a papular rash, followed by development of malaise, fever (a body temperature of 38° C. (100° F.), but may be as high as 42° C. (108° F.) in rare cases), and anorexia. Typically, the disease is more severe in adults. Chickenpox is rarely fatal, although it is generally more severe in adult males than in adult females or children. Pregnant women and those with a suppressed immune system are at highest risk of serious complications. The most common late complication of chickenpox is shingles, caused by reactivation of the varicella zoster virus decades after the initial episode of chickenpox.

Polyoma viruses are DNA-based, small (40-50 nm in diameter) and icosahedral in shape and do not have a lipoprotein envelope. JV virus can infect the respiratory system, kidneys or brain. BK virus produces a mild respiratory infection and can affect the kidneys of immunosuppressed transplant patients. Both of these polyoma viruses are widespread and are highly common in childhood and young adult infections.

SUMMARY OF THE INVENTION

Described herein is a method of treating a viral infection selected from the group consisting of an adenoviral infection, a polyoma virus infection, a human papilloma virus infection, and a pox virus infection in a subject comprising administering ethyl mercury or thiol derivative or salts thereof to the subject in an amount effective to treat the viral infection. In some embodiments, the treatment is a prophylactic treatment.

In another aspect, described herein is a method of reducing the infectivity of a virus selected from the group consisting of an adenovirus, a polyoma virus, a human papilloma virus, and a pox virus comprising contacting the virus with ethyl mercury or thiol derivative for salts thereof in an amount effective to reduce the infectivity of the virus.

In some embodiments, the thiol derivative of ethyl mercury is selected from the group consisting of an alkylthiol-ethyl mercury derivative and an arylthiol ethyl mercury derivative. In one embodiment, the thiol derivative of ethyl mercury is thimerosal. The term "thiol derivative of ethyl mercury" as used herein means a compound having a mercury sulfur bond and capable of releasing ethyl mercury or providing comparable therapeutic effects.

In some embodiments, the administration step comprises a route of administration selected from the group consisting of sublingual and subcutaneous administration.

In one embodiment, the thimerosal is administered in a dosage of about 0.05 μg to about 500 μg. In another embodiment, the thimerosal is administered in a dosage of about 0.05 μg to about 50 μg. In yet another embodiment, the thimerosal is administered in a dosage of about 0.2 μg. In another embodiment, thimerosal is administered sublingually as a drop (in a dose of 0.05 cc in a pharmaceutically acceptable carrier or excipient). In some embodiments, thimerosal is administered at least three times a day.

The subjects treated in the methods disclosed herein in its many embodiments are desirably human subjects, although it is to be understood that the principles of the presently disclosed subject matter indicate that the presently disclosed subject matter is effective with respect to invertebrate and to all vertebrate species, including mammals, which are intended to be included in the term "subject". Moreover, a mammal is understood to include any mammalian species in which treatment or prevention of a viral infection described herein is desirable, particularly agricultural and domestic mammalian species.

DETAILED DESCRIPTION

Figure 1:
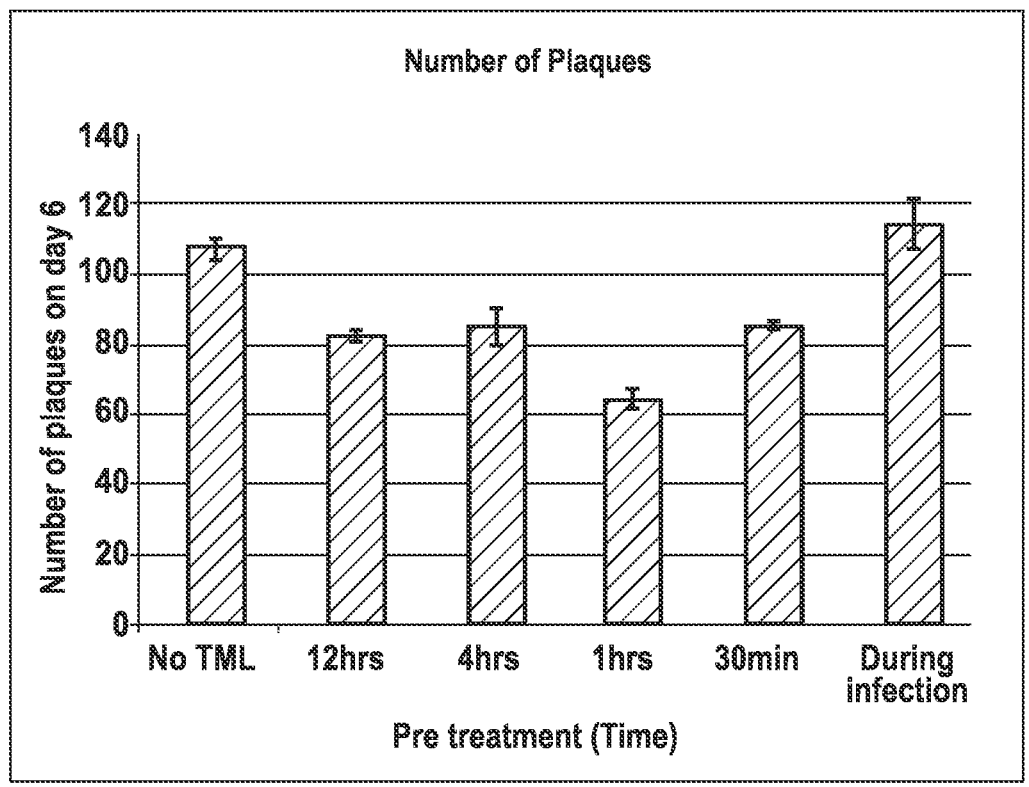
FIG. 1 is a graph shows the number of plaques formed on day 6 post-infection of Vero cells with HSV after prophylactic treatment with thimerosal at various time points.

The present application is based on the discovery that a thiol derivative of ethyl mercury down-regulated expression of various tubulin-associated genes. Because various viruses, including adenoviruses, hepnadenoviruses, herpes viruses, polyomaviruses, influenza viruses and papillomaviruses utilize the host cytoskeleton (including microtubules) to gain entry into a host cell's nucleus, the down-regulation of tubulin-associated genes, without being bound to any particular theory, interferes with the virus' ability to enter the nucleus, thus preventing further replication of the virus and the amelioration of the viral infection.

Thus, in one aspect, described herein is a method of treating a viral infection selected from the group consisting of an adenoviral infection, a human papillomavirus infection, a polyoma virus and a poxvirus infection in a subject comprising administering ethyl mercury or thiol derivative or salts thereof to the subject in an amount effective to treat the viral infection.

In some embodiments, the thiol derivative of ethyl mercury is selected from the group consisting of an alkylthiolethyl mercury derivative and an arylthiol ethyl mercury derivative.

As used herein, the term "alkyl" refers to straight chained and branched hydrocarbon groups, nonlimiting examples of which include methyl, ethyl, and straight chain and branched propyl and butyl groups. The term "alkyl" includes "bridged alkyl," i.e., a bicyclic or polycyclic hydrocarbon group, for example, norbornyl, adamantyl, bicyclo[2.2.2]octyl, bicyclo [2.2.1]heptyl, bicyclo[3.2.1]octyl, or decahydronaphthyl. Alkyl groups optionally can be substituted, for example, with hydroxy (OH), halo, aryl, heteroaryl, ester, carboxylic acid, amide, guanidine, and amino.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The salts, e.g., pharmaceutically acceptable salts, of the compounds of ethyl mercury or thiol derivatives thereof may be prepared by reacting the appropriate base or acid with a stoichiometric equivalent of the ethyl mercury or derivative thereof. Similarly, pharmaceutically acceptable derivatives (e.g., esters), metabolites, hydrates, solvates and prodrugs of ethyl mercury may be prepared by methods generally known to those skilled in the art. Thus, another embodiment provides compounds that are prodrugs of ethyl mercury. In general, a prodrug is a compound which is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of ethyl mercury. Examples of pharmaceutically-acceptable prodrug types are described in Higuchi and Stella, Pro-drugs as Novel Delivery Systems, Vol. 14 of the A.C.S. Symposium Series, and in Roche, ed., Bioreversible Carriers in Drug Design, American Pharmaceutical Association and Pergamon Press, 1987, both of which are incorporated herein by reference.

The compounds and compositions described herein may also include metabolites. As used herein, the term "metabolite" means a product of metabolism of a compound of the embodiments or a pharmaceutically acceptable salt, analog, or derivative thereof, that exhibits a similar activity in vitro or in vivo to ethyl mercury. The compounds and compositions described herein may also include hydrates and solvates. As used herein, the term "solvate" refers to a complex formed by a solute (herein, ethyl mercury) and a solvent. Such solvents for the purpose of the embodiments preferably should not negatively interfere with the biological activity of the solute. Solvents may be, by way of example, water, ethanol, or acetic acid. In view of the foregoing, reference herein to a particular compound or genus of compounds will be understood to include the various forms described above, including pharmaceutically acceptable salts, esters, prodrugs, metabolites and solvates thereof.

Appropriate dosages may be ascertained through the use of established assays for determining dose-response and toxicity and side-effect data. Typically, a pharmaceutical dosage unit for the delivery of ethyl mercury or thiol derivative thereof comprises a liquid or solid carrier and an effective amount of ethyl mercury or thiol derivative thereof to treat a viral infection described herein. One suitable carrier for sublingual administration comprises a phenylated saline solution. In one embodiment, the thiol derivative of ethyl mercury is thimerosal. Effective amounts of thimerosal range from about 0.05 µg to 500 µg thimerosal with about 0.1 µg to about 50 µg thimerosal being preferred and about 0.2 µg thimerosal being particularly preferred.

In some embodiments, thimerosal is administered 1, 2, 3, 4, 5, 6, 7, 8, 9, 10 or more times daily for a period of 1, 2, 3, 4, 5, 6 or more weeks. Additional therapy may be administered on a period basis, for example, daily, weekly or monthly.

In some embodiments, the ethyl mercury (or thiol derivative or salts thereof) is formulated in compositions that include at least one pharmaceutically acceptable carrier or excipient. Generally, this entails preparing compositions that are essentially free of pyrogens, as well as other impurities that could be harmful to humans or animals.

As used herein, "pharmaceutically acceptable carrier or excipient" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

In some embodiments, the administration of ethyl mercury (or thiol derivative or salts thereof) is carried out in a variety of conventional ways, including, but not limited to, oral ingestion, sublingual application, subcutaneous, intraperitoneal, and parenteral or intravenous injection. Sublingual administration to the subject is preferred. The treatment may consist of a single dose or a plurality of doses over a period of time.

For oral administration, ethyl mercury (or thiol derivatives or salts thereof) can be combined with pharmaceutically-acceptable carriers well known in the art. Such carriers enable the compound to be formulated as tablets, pills, dragees, capsules, liquids, gels, syrups, slurries, suspensions and the like, for oral ingestion by a subject to be treated.

Pharmaceutical preparations for oral use can be obtained using a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures.

Formulations for parenteral administration include aqueous solutions of ethyl mercury (or thiol derivative or salts thereof). Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the ethyl mercury (or thiol derivative or salts thereof) may be in powder form for constitution with a suitable vehicle, e.g., sterile pyrogen free water, before use.

The compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The following examples are illustrative and are not intended to limit either the scope or spirit of the invention.

Example 1

A two year old cat presented with decreased appetite, lethargy and excessive salivation. Practioners suspected adenovirus, calcivirus, or rhinotracheitis virus, with adenovirus being the lead suspect. The cat was treated with thimerosal at a rate of two drops (in a dose of 0.05 cc per drop) three times a day. Symptoms were resolved on the first day of treatment.

Example 2

A second cat in the same household developed the same symptoms and received the same treatment described in Example 1. The second cat showed a rapid and complete response to thimerosal therapy.

Example 3

A fifty-five year old mother shared a drink with her twenty-one year old daughter. Later that day the daughter asked her mother, who is an RN, to check the daughter's glands as they felt swollen and her throat hurt. Daughter was given one drop (in a dose of 0.05 cc) of thimerosal at a two hour interval and the symptoms were resolved. The mother was also dosed with thimerosal as a prophylactic measure and did not develop any symptoms.

Example 4

A fifty-three old male with classic symptoms of the common cold used one drop of thimerosal (in a dose of 0.05 cc) every hour for one day. Symptoms were resolved by the next day.

Example 5

The nine year old son of the male in Example 4 was treated with thimerosal for the common cold on several occasions. The son experienced symptoms for 5-7 days without treatment, which was reduced to 1-3 days when treated with thimerosal.

Example 6

A sixty year old female with symptoms of an adenovirus infection took one drop of thimerosal (in a dose of 0.05 cc) every 15 minutes for an hour, and then one drop every hour until bedtime. The symptoms were significantly reduced and were gone the next day.

Example 7

Several children suffering from molluscum contagiosum, a poxvirus infection, have been successfully treated with one drop of thimerosal (in a dose of 0.05 cc) every 15 minutes for an hour and then one drop every hour until bedtime. Thimerosal was administered in one drop every six times daily on days 2 and 3 and then as needed on subsequent days.

Example 8

A three year old girl suffering from laryngeal papillomas spreading to the soft palate was treated with one drop of thimerosal (in a dose of 0.05 cc) every 15 minutes for an hour and then one drop every hour until bedtime. Thimerosal was administered in one drop every six times daily on days 2 and 3 and then as needed on subsequent days. Resolution of the symptoms was complete in five days.

Example 9

The following Example demonstrates the anti-viral activity of thimerosal in cell culture models.

Primary normal human keratinocyte (NHEK) cells were purchased from Invitrogen (Carlsbad, Calif.) and maintained according to the supplier's instructions. "HSV latent infection" PCR arrays were obtained from Applied Biosystems (Carlsbad, Calif.). Expressions of a total of 27 HSV1 latent infection-related genes and 3 different housekeeping genes were determined after 24 hours of treatment of NHEK cells with thimerosal at concentrations of 0.004, 0.04, 0.4, 4 or 0 µM. Table 1 below displays the genes that were up- and down-regulated upon thimerosal treatment. The values in Table 1 have been normalized to saline-treated control cells and $p<0.05$ was the cut-off for statistical significance.

TABLE 1

| Gene | Fold changes (vs. Control) | | | | p-values | | | |
| --- | --- | --- | --- | --- | --- | --- | --- | --- |
| | 0.004 µM | 0.04 µM | 0.4 µM | 4 µM | 0.004 µM | 0.04 µM | 0.4 µM | 4 µM |
| POLR2A | −1.84 | −1.84 | — | −1.84 | 0.00001 | 0.000005 | >0.05 | >0.05 |
| LAT-SPNS1 | — | — | 1.87 | — | >0.05 | >0.05 | 0.00024 | >0.05 |
| SP1 | — | 1.95 | 2.04 | 2 | >0.05 | 0.000051 | 0.000004 | 0.00004 |
| TUBA4A | — | 1.96 | 2 | 1.95 | >0.05 | 0.000187 | 0.00004 | 0.0001 |
| TUBB4 | — | 2.13 | 2.12 | — | >0.05 | 0.00189 | 0.000284 | >0.05 |
| TUBB4Q | — | — | 1.85 | — | >0.05 | >0.05 | 0.000627 | >0.05 |
| TUBE1 | — | 1.95 | 2.03 | 1.98 | >0.05 | 0.00131 | 0.00001 | 0.000037 |

Results: Thimerosal treatment increases the mRNA levels for the various microtubule isoforms indicating that thimerosal is able to regulate the activity of genes that are essential for cellular cytoskeletal structure. Additionally, thimerosal treatment down-regulated the expression of POLR2A (see Table 1), a gene that encodes for the large subunit of RNA polymerase II, possible leading to a stall in the transcriptional activity of the host genome. While results indicated an increase in the expression of transcription factor SP1 that may selectively turn on various genes, the increase in the expression of LAT-SPNS1 may regulate autophagic cell death pathway.

Discussion: Thimerosal's ability to alter intracellular calcium ion concentration by acting like an oxidizing agent is a great deal of interest in reproductive biology. Thimerosal treatment alone arrests oocytes in metaphase, probably by oxidizing tubulin sulfhydryl groups and thus destroying the spindles. However, a 10 minute exposure to 200 µM thimerosal followed by a 30 minute incubtation in 8 mM DTT induced complete activation of porcine oocytes leading to formation of pronuclei (Machaty, Biol. Reprod., 57:1123-1127, 1997).

Viruses utilize cytoskeletal filaments to hitchhike rides to difference subcellular locations in order to replicate and package viral genomes. Without being bound by any particular theory, it is contemplated that thimerosal oxidizes tubulin sulfydryl groups thus preventing microtubule formation which is most likely necessary for the establishment of latent infections and reactivations to cause recurrent or new episodes of the disease.

Example 10

The following Example demonstrates that prophylactic treatment with thimerosal reduced viral production in Vero cells.

Green Monkey Kidney (Vero) cells were treated with thimerosal (40 ng/ml) at various time points (12 hours, 4 hours, 1 hour, and 30 minutes) prior to and at the time of HSV infection. The number of plaques formed on day 6 post-infection was used to measure the effectiveness of thimerosal in preventing HSV infections. The results are set forth in FIG. 1.

The results indicate that prophylactic therapy with thimerosal resulted in a significant decrease in the number of plaques formed on day 6 post-infection. While treatment with thimerosal 1 hour prior to HSV infection caused the highest reduction in the plaque number, all other time points demonstrated that thimerosal has anti-viral activity. Treatment with thimerosal at the time of infection did not reduce the number of plaques suggesting that thimerosal does not directly interact with the virus particles. Without being bound by any particular theory, it is contemplated that thimerosal interferes with cellular machinery that effects the infection, replication and packaging of HSV for virion production and propagation.

Example 11

The following Example demonstrates that treatment with thimerosal after HSV infection reduced viral production in Vero cells.

Figure 2:
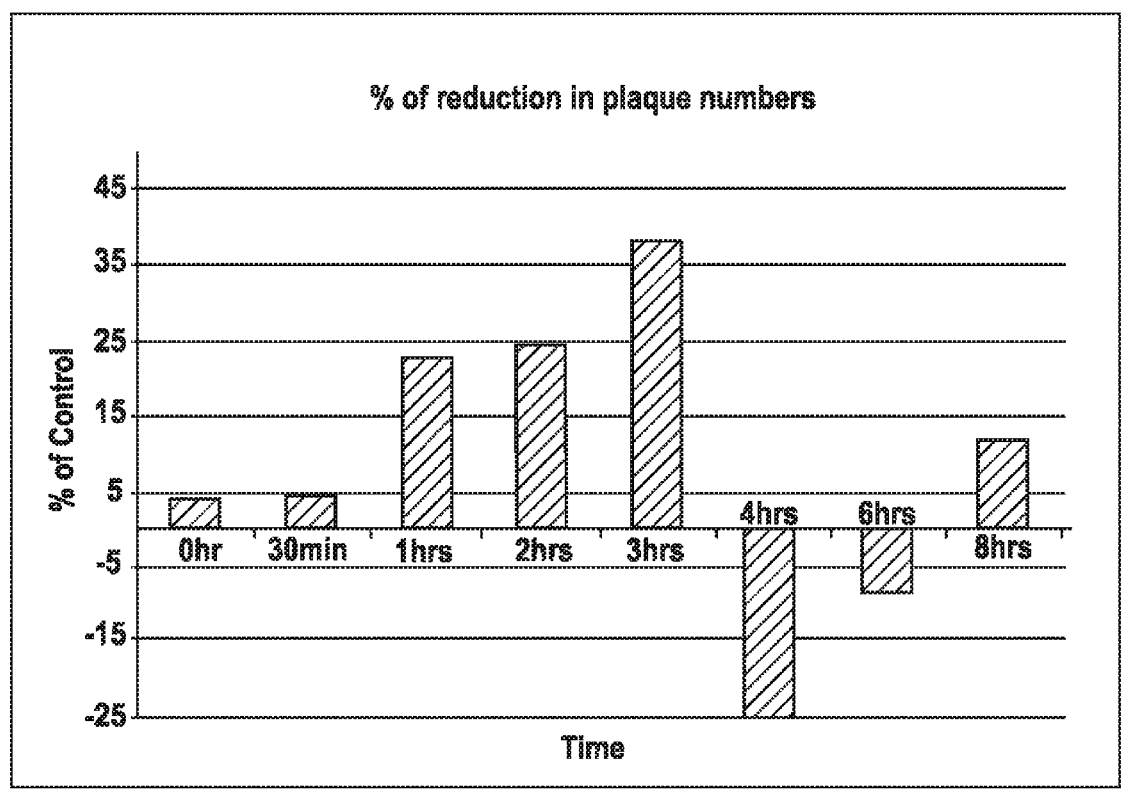
FIG. 2 shows the percent inhibition of HSV infection after treatment with thimerosal at various time points.

Green Monkey Kidney (Vero) cells were treated with thimerosal (40 ng/ml) at various time points (30 minutes, 1 hour, 2 hours, 3, hours, 4 hours, 6 hours and 8 hours) after HSV infection. The number of plaques formed on day 6 post-infection was used to measure the effectiveness of thimerosal in preventing HSV infections. The number of plaques was normalized to the number of plaques in the control. FIG. 2 shows the percent inhibition as the percent of control.

The results indicate that thimerosal treatment after HSV infection resulted in a significant decrease in the number of plaques form on day 6 post-infection. Interestingly, while post-infection treatment with thimerosal from 1-3 hours cause a significant reduction in the plaque numbers, all other time points showed that thimerosal did not significantly reduce the number of plaques. Treatment with thimerosal at the time of infection did not change the number of plaques, suggesting that thimerosal does not interact directly with the virus particles. Without being bound to any particular theory, it is contemplated that between the time points 1-3 hours thimerosal interferes with cellular machinery that effects infection, replication and packaging of HSV for virion production and propagation.

Example 12

The following Example demonstrates that continuous treatment with thimerosal after HSV infection reduced viral production in ARPE-19 cells.

Figure 3:
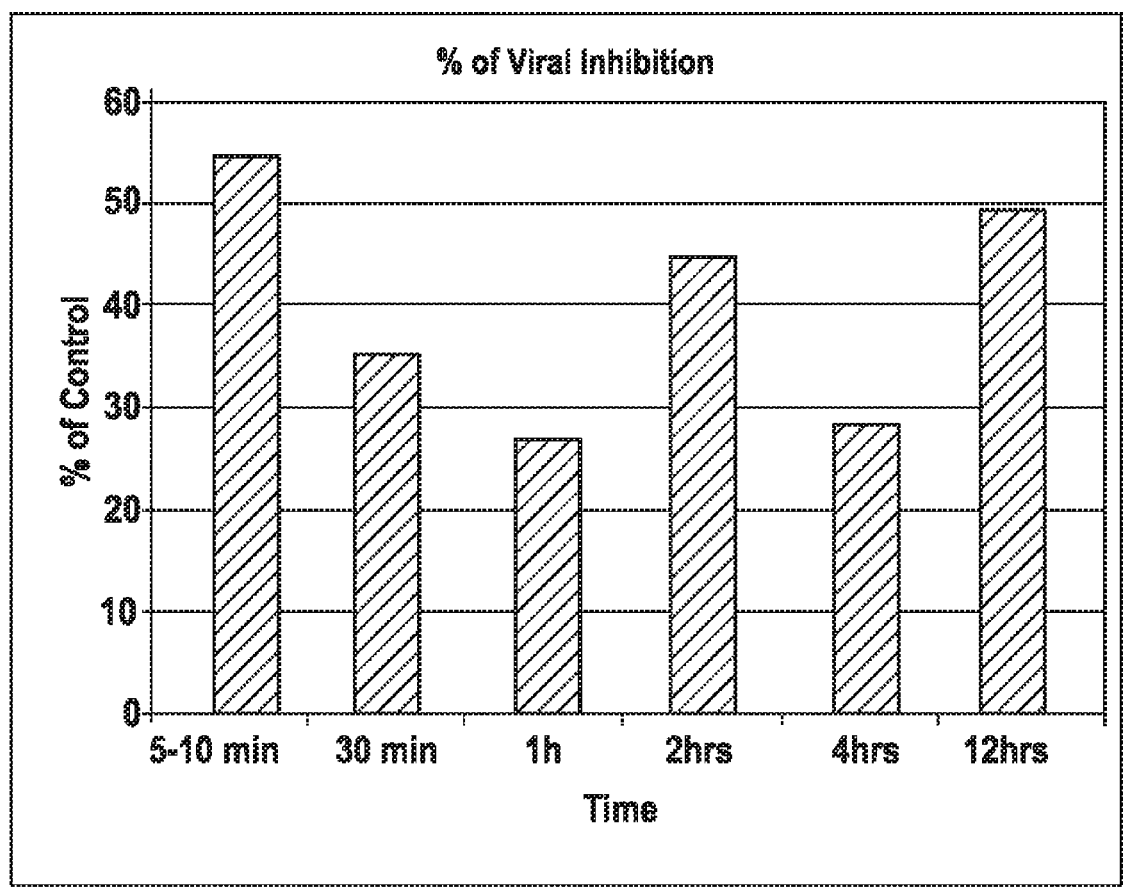
FIG. 3 shows the percent inhibition of HSV infection after prophylactic treatment with thimerosal at various time points.

Human retinal pigment epithelial (ARPE-19) cells were treated with thimerosal (40 ng/ml) at various time points (12 hours, 4 hours, 2 hours, 1 hour, 30 minutes and 5-10 minutes) prior to HSV infection. The number of plaques formed on day 6 post-infection was used to measure the effectiveness of thimerosal in preventing HSV infections. The number of plaques was normalized to the number of plaques in the control. FIG. 3 shows the percent inhibition as the percent of control.

Results indicate that continuous treatment of ARPE-19 cells before HSV infection demonstrated that the results set forth in Example 11 were reproducible in human cells and that thimerosal was able to inhibit the activity of HSV up to 55% depending on the treatment time point.

Example 13

The following Example investigated the role of human peripheral blood mononuclear cell (PMBC) media on the anti-viral activity of thimerosal.

PBMCs were incubated with 40 ng/ml thimerosal for a minimum of 6 hours and then were overlaid in ARPE-19 cells at various time points (12 hours, 4 hours, 2 hours, 1 hour, 30 minutes and 10 minutes) prior to HSV infection of the ARPE-19 cells. ARPE-19 cells were not continuously treated with thimerosal. ARPE-19 cells receiving thimerosal treatment with PBMC media was used as a control. The number of plaques formed on day 6 post-infection was used to measure the effectiveness of thimerosal in preventing HSV infections. The number of plaques was normalized to the number of plaques in the control.

The results indicated that thimerosal in combination with PBMC media demonstrated a stronger antiviral activity that thimerosal alone. Without being bound to any particular theory, it is contemplated that PBMCs secrete various cytokines into the medium that enhance the anti-viral activity of thimerosal.

Example 14

The following Example demonstrates that prophylactic treatment with thimerosal reduced the infectivity of a polyoma virus in Vero cells.

Vero cells were plated to a density of 70% confluency in 96-well dishes at a concentration of 75,000 cells/well). Cells were pretreated with either 40 ng or 80 ng thimerosal in 100 µl media for either 1 hour, 2 hours, 3 hours, 4 hours or 16 hours prior to infection.

20 minutes prior to infection, the cells were cooled to 4° C. on ice. Media containing the thimerosal was then removed and replaced with infection media (30 µl per well of a 1:100 dilution of JC virus (stock titer=7.9×10$^6$) or a 1:50 dilution of BK virus (stock titer=8.3×10$^5$)). Plates were left on ice for 20 additional minutes and then incubated at 37° C. for 1 hour to allow infection to proceed. The plates were rocked every 15 minutes to distribute the virus.

After 1 hour at 37° C., virus was removed and cells were washed with unsupplemented MEM to remove unbound virus. The cells were then fed 100 µl/well complete media and stained for Tad (BK virus) or V-ag (JC virus) and scored via direct immunofluorescence. The thimerosal doses tested did not appear to be toxic in either cell type.

Figure 4A:
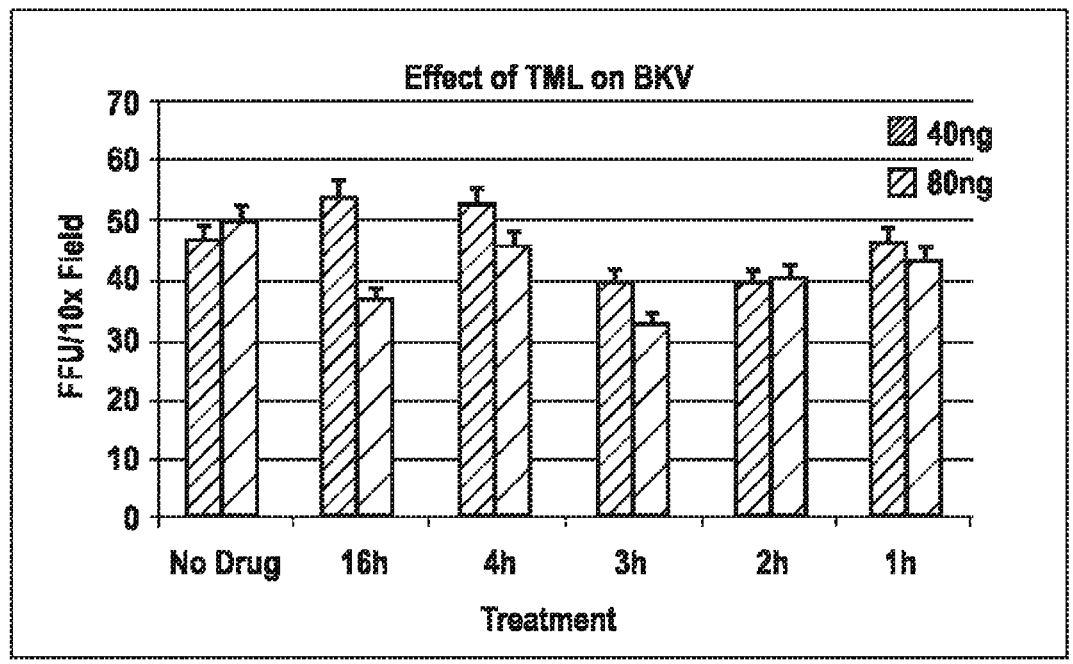
FIG. 4A and FIG. 4B show the effect of thimerosal (40 ng and 80 ng) on the infectivity of the BK virus (BKV) and JC virus (JCV), respectively, at various time points.
Figure 4B:
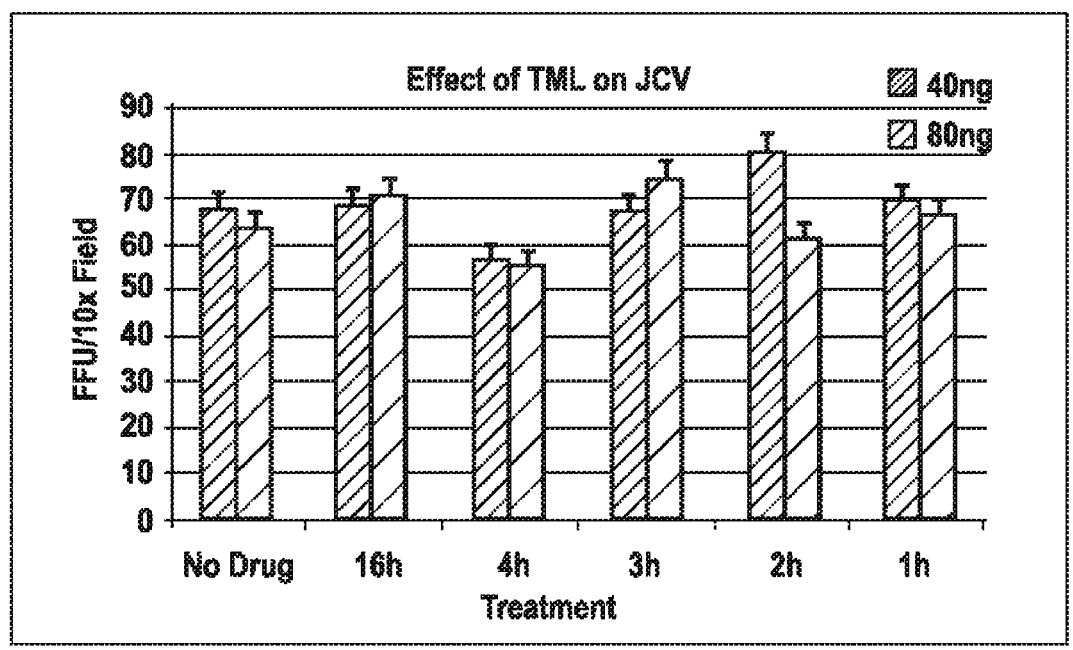

Results indicated that pre-treatment with thimerosal (80 ng/ml) at all time points except 2 hours prior to BK virus infection resulted in a reduction of the infectivity of the virus. See FIG. 4. The highest reduction (approximately 30%) was observed when pretreated with thimerosal (80 ng/ml) for 16 hours prior to BK virus infection. Thimerosal pre-treatment did not appear to inhibit infectivity of the JC virus.

Example 15

The following Example investigates the ability of thimerosal to reduce the infectivity of the BK virus in Vero cells when treated with thimerosal at extremely high and low doses at various time points.

24 hours prior to infection Vero cells were plated to a density of 70% confluency in 48-well dishes. Cells were treated with either 4 ng/ml, 8 ng/ml, 400 ng/ml or 800 ng/ml thimerosal at the time of infection, 30 minutes, 1 hour or 3 hours post-infection.

20 minutes prior to infection, the plates were cooled to 4° C. on ice. Media containing the thimerosal was then removed and replaced with infection media (49 µl per well MEM/2% FBS/1% pen-strep+1 µl BK virus (stock titer=7.7×10$^5$)). Plates were left on ice for 20 additional minutes and then incubated at 37° C. for 1 hour to allow infection to proceed. The plates were rocked every 15 minutes to distribute the virus.

After 1 hour at 37° C., virus was removed and cells were washed with unsupplemented MEM to remove unbound virus. The cells were then fed 0.5 ml/well complete media. Cells were continuously treated with thimerosal and stained 48 hours post-infection for T-ag expression (BK virus) via indirect immunofluorescence.

Figure 5:
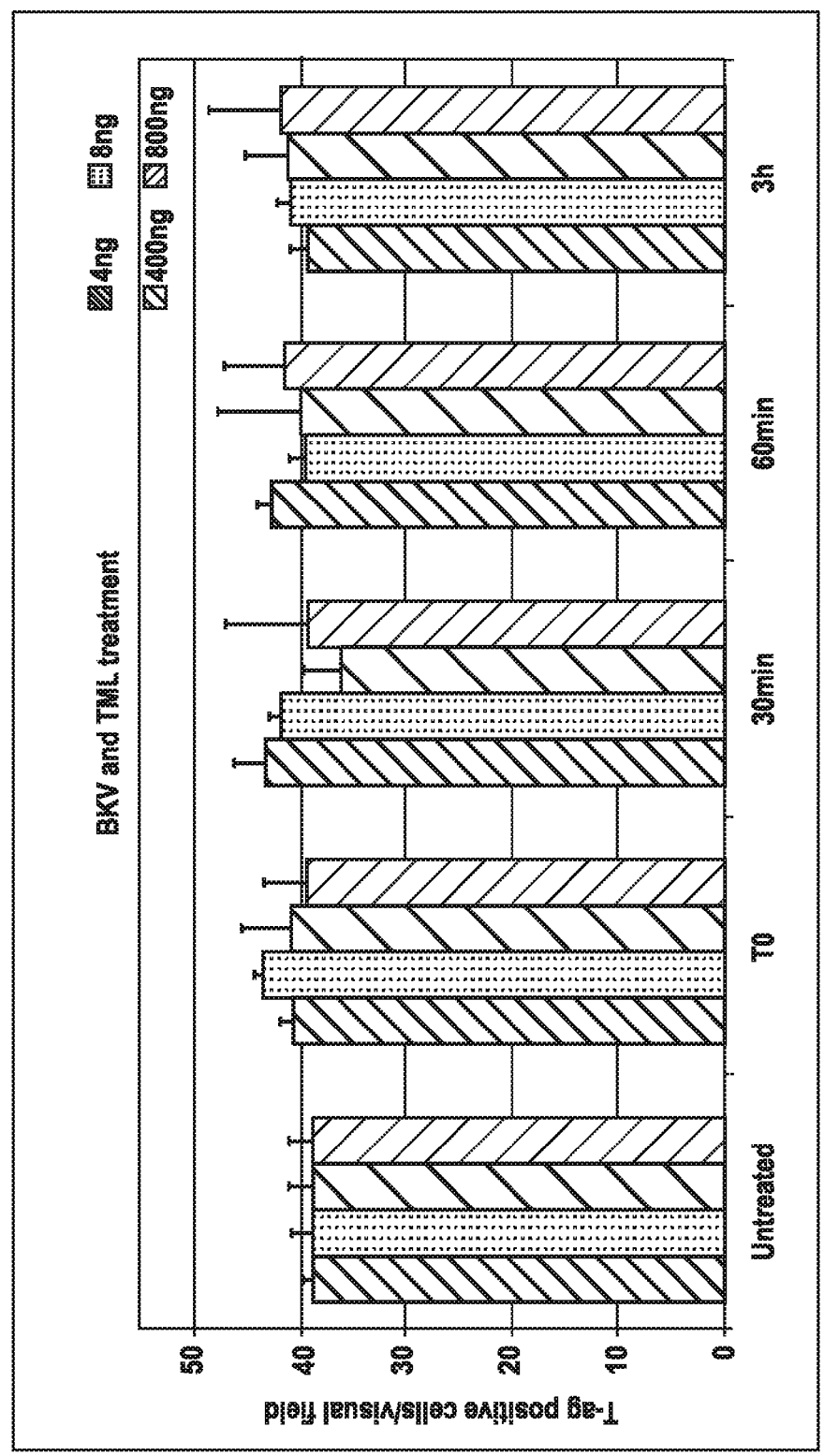
FIG. 5 shows the effect of thimerosal at various concentrations on the infectivity of the BK virus (BKV) at various time points.

Results indicated that treatment with thimerosal (400 ng/ml) at 30 minutes post-infection resulted in a reduction of the infectivity of the virus. See FIG. 5. The higher doses of thimerosal appeared to be toxic.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method of treating a viral infection selected from the group consisting of an adenoviral infection, a human papilloma virus infection, a polyoma virus infection and a pox virus infection in a subject comprising systemically administering ethyl mercury or thiol derivative thereof to the subject at a dosage range of about 0.05 µg to about 500 µg effective to treat the viral infection.

2. The method of claim 1, wherein the thiol derivative of ethyl mercury is thimerosal.

3. The method of claim 2, wherein the subject is human.

4. The method of claim 3, wherein the administering step comprises a route of administration selected from the group consisting of sublingual and subcutaneous administration.

5. The method of claim 1, wherein the ethyl mercury or thiol derivative thereof is administered sublingually.

6. The method of claim 1, wherein the ethyl mercury or thiol derivative is administered at a dosage range of about 0.2 µg to about 50 µg.

7. The method of claim 1, wherein the ethyl mercury or thiol derivative is administered at a dose of about 0.2 µg.

8. The method of claim 5, wherein the ethyl mercury or thiol derivative is administered in one drop intervals at least three times a day.

* * * * *